(12) United States Patent
Norton et al.

(10) Patent No.: US 9,423,348 B2
(45) Date of Patent: Aug. 23, 2016

(54) ABSORBANCE SPECTRUM SCANNING FLOW CYTOMETRY

(75) Inventors: Pierce O. Norton, Los Gatos, CA (US);
Yong Qin Chen, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 169 days.

(21) Appl. No.: 14/123,630

(22) PCT Filed: May 31, 2012

(86) PCT No.: PCT/US2012/040126
§ 371 (c)(1),
(2), (4) Date: Dec. 3, 2013

(87) PCT Pub. No.: WO2012/177367
PCT Pub. Date: Dec. 27, 2012

(65) Prior Publication Data
US 2014/0093949 A1    Apr. 3, 2014

Related U.S. Application Data

(60) Provisional application No. 61/500,707, filed on Jun. 24, 2011, provisional application No. 61/557,334, filed on Nov. 8, 2011.

(51) Int. Cl.
*G01N 21/64* (2006.01)
*G01N 15/14* (2006.01)
*G01N 15/10* (2006.01)

(52) U.S. Cl.
CPC ............ *G01N 21/64* (2013.01); *G01N 15/1434* (2013.01); *G01N 15/1459* (2013.01); *G01N 2015/1006* (2013.01); *G01N 2015/1438* (2013.01); *G01N 2015/1477* (2013.01)

(58) Field of Classification Search
CPC ............ G01N 15/1434; G01N 15/147; G01N 15/1459; G01N 2021/6419; G01N 2021/6421; G01N 21/64; G01N 2015/1438; G01N 2015/1006; G01N 2015/1477; G01J 3/0208; G01J 3/10; G01J 3/36; G01J 3/14
See application file for complete search history.

(56) References Cited

U.S. PATENT DOCUMENTS 3,062,963 A   11/1962  Douty
3,470,373 A   9/1969   Brewer et al.
(Continued)

FOREIGN PATENT DOCUMENTS

CN    1282378 A      1/2001
CN    101713723 A    5/2010
(Continued)

OTHER PUBLICATIONS

Telford et al., "Supercontinuum white light lasers for flow cytometry", Cytometry A; May 2009; 75(5):450-459.
(Continued)

*Primary Examiner* — Gail R Gabel
(74) *Attorney, Agent, or Firm* — Bret E. Field; Bozicevic, Field & Francis LLP

(57) ABSTRACT

The present invention provides systems and methods for analyzing the excitation spectra of fluorescent particles in a flowing stream. The system uses a white light laser and color separation optics to provide a spatially-distributed, continuous color-spectrum excitation light system that is used to illuminate a region of a flowing stream. A particle that passes through the detection region traverses the full dispersed spectrum of excitation light, and the fluorescence emissions from the particle are continuously measured as it passes through the detection region. The measured fluorescence emissions at each wavelength of excitation light, which changes through full spectrum of the excitation light as the particle passes through the detection region, provides the excitation spectrum of the particle.

15 Claims, 12 Drawing Sheets

(56) References Cited

U.S. PATENT DOCUMENTS

| | | |
|---|---|---|
| 3,497,690 A | 2/1970 | Wheeless, Jr. et al. |
| 3,916,197 A | 10/1975 | Fulwyler |
| 4,609,286 A | 9/1986 | Sage, Jr. |
| 4,786,165 A | 11/1988 | Yamamoto et al. |
| 4,845,653 A | 7/1989 | Conrad et al. |
| 5,599,717 A | 2/1997 | Vo-Dinh |
| 5,627,040 A | 5/1997 | Bierre et al. |
| 5,739,000 A | 4/1998 | Bierre et al. |
| 5,760,900 A | 6/1998 | Ito et al. |
| 5,795,727 A | 8/1998 | Bierre et al. |
| 5,962,238 A | 10/1999 | Sizto et al. |
| 6,014,904 A | 1/2000 | Lock |
| 6,683,314 B2 | 1/2004 | Oostman, Jr. et al. |
| 6,944,338 B2 | 9/2005 | Lock et al. |
| 7,129,505 B2 | 10/2006 | Oostman, Jr. et al. |
| 9,103,721 B2 * | 8/2015 | Raicu .................. G02B 21/002 356/300 |

FOREIGN PATENT DOCUMENTS

| | | |
|---|---|---|
| EP | 1403632 A1 | 3/2004 |
| EP | 2327977 A2 | 6/2011 |

OTHER PUBLICATIONS

Robinson et al., "Multi-Spectral cytometry of single bio-particles using a 32-channel detector", Advanced Biomedical and Clinical Dianostic Systems III, edited by Tuan Vo-Dinh et al., Proc. of SPIE vol. 5692 (SPIE, Bellingham, WA, 2005): p. 359-365.

* cited by examiner

Start Spectral Scan

End Spectral Scan

Trigger

Start Spectral Scan red
green
yellow
blue red
green
yellow
blue

End Spectral Scan

Excitation Wavelengths (nm)

ABSORBANCE SPECTRUM SCANNING FLOW CYTOMETRY

BACKGROUND OF THE INVENTION

1. Field of the Invention

The present invention relates to the field of optical analysis of fluorescent particles in fluid streams.

2. Description of Related Art

Flow-type particle analyzers, such as flow cytometers, are well known analytical tools that enable the characterization of particles on the basis of optical parameters such as light scatter and fluorescence. In a flow cytometer, for example, particles, such as molecules, analyte-bound beads, or individual cells, in a fluid suspension are passed by a detection region in which the particles are exposed to an excitation light, typically from one or more lasers, and the light scattering and fluorescence properties of the particles are measured. Particles or components thereof typically are labeled with fluorescent dyes to facilitate detection, and a multiplicity of different particles or components may be simultaneously detected by using spectrally distinct fluorescent dyes to label the different particles or components. Typically, a multiplicity of photodetectors, one for each of the scatter parameters to be measured, and one for each of the distinct dyes to be detected. The data obtained comprise the signals measured for each of the light scatter parameters and the fluorescence emissions.

Cytometers further comprise means for recording the measured data and analyzing the data. For example, typically, data storage and analysis is carried out using a computer connected to the detection electronics. The data typically are stored in tabular form, wherein each row corresponds to data for one particle, and the columns correspond to each of the measured parameters. The use of standard file formats, such as an "FCS" file format, for storing data from a flow cytometer facilitates analyzing data using separate programs and machines. Using current analysis methods, the data typically are displayed in 2-dimensional (2D) plots for ease of visualization, but other methods may be used to visualize multidimensional data.

The parameters measured using a flow cytometer typically include the excitation light that is scattered by the particle along a mostly forward direction, referred to as forward scatter (FSC), the excitation light that is scattered by the particle in a mostly sideways direction, referred to as side scatter (SSC), and the light emitted from fluorescent molecules in one or more channels (range of frequencies) of the spectrum, referred to as FL1, FL2, etc., or by the fluorescent dye that is primarily detected in that channel Different cell types can be identified by the scatter parameters and the fluorescence emissions resulting from labeling various cell proteins with dye-labeled antibodies.

Flow cytometers are commercially available from, for example, BD Biosciences (San Jose, Calif.). Flow cytometry is described at length in the extensive literature in this field, including, for example, Landy et al. (eds.), Clinical Flow Cytometry, Annals of the New York Academy of Sciences Volume 677 (1993); Bauer et al. (eds), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Shapiro, Practical Flow Cytometry, 4th ed., Wiley-Liss (2003); all incorporated herein by reference. The data obtained from an analysis of cells (or other particles) by multi-color flow cytometry are multidimensional, wherein each cell corresponds to a point in a multidimensional space defined by the parameters measured. Populations of cells or particles are identified as clusters of points in the data space. The identification of clusters and, thereby, populations can be carried out manually by drawing a gate around a population displayed in one or more 2-dimensional plots, referred to as "scatter plots" or "dot plots, of the data. Alternatively, clusters can be identified, and gates that define the limits of the populations, can be determined automatically. A number of methods for automated gating have been described in the literature. See, for example, U.S. Pat. Nos. 4,845,653; 5,627,040; 5,739,000; 5,795,727; 5,962,238; 6,014,904; 6,944,338, each incorporated herein by reference.

In a typical laser-based flow cytometer, the excitation wavelengths available are limited by the availability of a suitable laser. Wavelength-selectable, single-wavelength excitation sources have been described for use in flow cytometry. For example, U.S. Pat. No. 4,609,286 (Sage) describes a flow cytometer that uses a dispersion prism to select a wavelength from a spectrally rich light source for use as the excitation source. The light source is dispersed by the prism such that the wavelength can be selected using a slit to allow only light of essentially a single wavelength through, block all other wavelengths. The desired wavelength can be selected by physically moving the slit to correspond to the desired wavelength in the spectrum.

Telford et al, 2009, Cytometry A 75(5):450-459, describes the use of a supercontinuum white light laser as an excitation source in flow cytometry. The supercontinuum white light laser emits continuously over a wide bandwidth ranging from the near-ultraviolet to the infrared, thus appearing white to the human eye. Telford et al. describe interposing an acoustooptical filter or a coated bandpass filter in front of the beam to isolate particular wavelength ranges, permitting the user to select bandwidths of interest from the supercontinuum. The resulting excitation source can be used to select any single excitation wavelength and bandwidth by using a filter with the desired color transmission requirements.

In a typical flow cytometer, fluorescence emissions are measured in a multiplicity of detection channels (each defined as a range of frequencies within the spectrum), wherein the emissions in each channel are measured using a single photodetector. Thus, each detector provides a single measure of a range of frequencies. Typically, the detector channels are selected such that each channel is optimized to detect emissions from one of the distinct dyes. Alternatively, the emission light can be measured using an array of detection channels such that each dye emissions are measured in more than one channel.

Robinson et al., in Advanced Biomedical and Clinical Diagnostic Systems III, edited by Tuan Vo-Dinh et al., Proc. of SPIE Vol. 5692 (SPIE, Bellingham, Wash., 2005): 3579-365, describes a flow cytometer detection system in which the emitted light is dispersed by diffraction grating onto a 32 channel PMT detector. Thus, fluorescence emissions are measured in 32 narrow, adjacent detection channels that together span a region of the spectrum. Instead of a single fluorescence intensity value for each dye, the data obtained using this system comprise, for each dye, intensity values for a multiplicity of adjacent detection channels. The set of measurements obtained from a dye across a multiplicity of spectrally adjacent detection channels depends on the emission spectrum of a dye.

BRIEF SUMMARY OF THE INVENTION

The present invention provides systems and methods for analyzing the excitation spectra of fluorescent particles in a flowing stream.

The system of the present invention uses a white light laser and color separation optics to provide a spatially-distributed, continuous color-spectrum excitation system that is used to illuminate a region of a flowing stream. The spectrum of the excitation light is spread out along the length of flow stream such that the spectrum is spread over a region that is significantly larger than the diameter of a particle to be detected. A particle flowing through the detection region will, at any one point, be excited by only a small range of wavelengths, but will be exposed to the full spectrum of the excitation light as it traverses the entire detection region. As a fluorescent particle travels through the excitation beam and is thereby excited by a continuously changing wavelength of the excitation light, a detector measures the fluorescence emissions from the particle, which vary in intensity according to the excitation efficiency at each wavelength. The result is a scan of the excitation spectrum of the particle.

Spatial expansion (spreading) of the excitation light spectrum is achieved by passing the light through color separation optics, e.g., a color dispersion element, such as a prism or diffraction grating. The color separation optics are oriented such that the spectrum is spread along the flow path, covering an elongated detection region. A particle flowing in the stream will be exposed to continuously varying wavelength light as it passes through the detection region.

In general, the spectrum can be spread along the flow path such that a moving particle will sweep through the excitation light spectrum from short to long wavelength, or from long to short wavelength. Preferably, the spectrum is spread along the flow path such that a moving particle will sweep through the excitation light spectrum from short to long wavelength.

In one embodiment, a single, broad-band detector is used to measure the emissions from the particles excited by the continuous-spectrum excitation beam as the particle passes through the detection region. Thus, the particle emissions are measured continuously as the particle is excited sequentially by the full spectrum of excitation light. The range of wavelengths detected by the single detector preferably is selected to be in a range in which the fluorescent particle emits, but is outside the excitation spectrum. Preferably, the detector is configured to measure all wavelengths that are longer than the longest excitation wavelength using an appropriate long-pass filter.

In another embodiment, the excitation light source includes a continuously variable, wavelength-selectable bandpass filter (tuneable filter) positioned between the white-light laser excitation light source and the color separation optics. The filter allows selecting any essentially single-color (a narrow band of wavelengths) excitation beam from the range of colors provided by the white-light laser. The essentially single-color excitation beam will illuminate a single spot within the detection region. Because the spectrum is spread out over the detection region by the color separation optics, and the angle of dispersion is depends on the color of the light, a change in the color of the excitation light selected by the filter also results in a change in the position of the illumination spot within the detection region.

The continuously variable, wavelength-selectable bandpass filter is configured to continuously vary the wavelength of the excitation light from one end of the spectrum to the other, which also results in a sweep of the illumination spot from one end of the detection region to the other. The rate of change of the filter is timed such that the illumination spot traversed the detection region at the same rate that a particle in the flow stream does. By initiating the spectral sweep when the particle enters the detection region, the particle will remain illuminated while it transverses the detection region, but with a continuously varying color of excitation light.

The continuously varying spectral sweep that is aligned with the particle flow enables sweeping through the spectrum using the particle motion, but limits the excitation light to just the particle and, perhaps, a limited surrounding region. This minimized that amount of stray excitation light that may result in signal noise in the detection channel.

In another embodiment, multiple broad-band detectors are used to measure the emissions from the particles excited by the continuous-spectrum excitation beam as the particle passes through the detection region. Each detection channel (range of frequencies measured by a detector) is selected such that each is outside at least a portion of the excitation spectrum, with successive detection channels staggered such that each starts with a longer wavelength and overlaps less of the excitation light spectrum.

The embodiments using staggered detection channels, preferably together with the tuneably filtered excitation light, enable detection of particle emissions that in wavelengths that overlap a portion of the excitation light spectrum. As a particle moves through the detection region and is illuminated with progressively longer wavelengths, detection channels that measure light of a wavelength longer that the wavelength of the excitation light can be used to detect particle emissions. When the excitation light wavelength is lengthened during the scan such that it overlaps a detection channel, that detection channel is no longer useful for measuring emission because the interference caused by the excitation light. At that point, emissions are detected by one or more of the remaining detection channels. Similarly, when the excitation light wavelength is lengthened during the scan such that it overlaps the second detection channel, that detection channel is no longer useful for measuring emission because the interference caused by the excitation light, and emissions are detected by one or more of the remaining detection channels. The final detection channel preferably measures all wavelengths that are longer than the longest excitation wavelength using an appropriate long-pass filter.

In another embodiment, multiple band-pass detectors are used to measure the emissions from the particles excited by the continuous-spectrum excitation beam as the particle passes through the detection region. Each detection channel (range of frequencies measured by a detector), which detects light over a selected band of wavelengths, is selected such that the detection channels do not overlap. Preferably, each detection channel will correspond approximately to the excitation spectrum maximum of a fluorescent dye that is being used to label particles, such that each detection channel measures primarily the emissions from one of the dyes. This enables relatively independent measurements of the excitation spectra of each of the dyes used to label a multiply labeled particle.

In another aspect, the present invention provides methods of analyzing fluorescent particles using the instruments of the invention.

The present methods and instruments may be used to analyze particles labeled with one or more dyes. For a singly dyed particle, the dye can be identified from the excitation spectrum pattern by, for example, matching the measured excitation spectrum to previously measured excitation spectra from the dyes that are used in the assay. For a multiply dyed particle, the dyes can be identified from the excitation spectrum pattern by fitting the measured excitation spectrum to a combination of previously measured excitation spectra. Various known "goodness of fit" algorithms are suitable for fitting a measured spectrum to a combination of known spectra.

DETAILED DESCRIPTION OF THE INVENTION

Figure 1A:
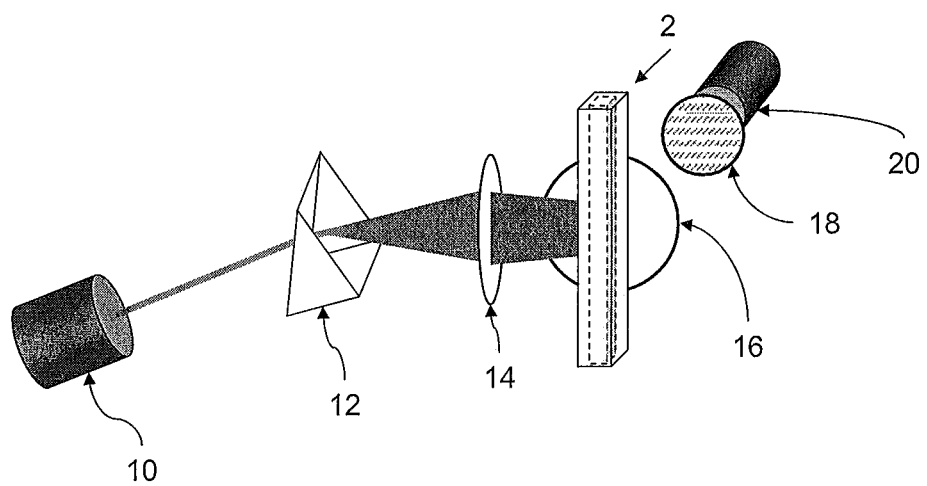
FIGS. 1A, 1B, and 1C depict schematic representations of elements of the optical system of an embodiment of a flow-type particle analyzer of the present invention.

The following definitions are provided for clarity. Unless otherwise indicated, all terms are used as is common in the art. All reference cited herein, both supra and infra, are incorporated herein by reference.

A "flow-type particle analyzer" is used herein to refers to any instrument that analyzes particles suspended in a flowing fluid stream by passing the particles past one or more optical detectors, and includes, for example, analyzing or sorting flow cytometers, hematology analyzers, and cell counters. The fluid particle-containing stream (flow stream) typically is passed through a channel in an optical cuvette in which optical analysis is carried out, although optical analysis can be carried out on a fluid stream in air, ejected from a nozzle. At least a portion, preferably all, of the cuvette and channel are optically transparent to enable optical detection of particles within the flow stream. For example, in a typical flow cytometer, optical detection is carried out by exciting fluorescently labeled particles using an excitation light from outside the cuvette, and the fluorescence emissions from the particles are detected using photodetectors positioned outside the cuvette. The optically transparent portion of a cuvette can be made from any suitable material, including fused silica, quartz, optical glass, or an optical grade plastic.

As used herein, "system" and "instrument" are intended to encompass both the hardware (e.g., mechanical and electronic) and associated software (e.g., computer programs) components.

A photodetector, as used herein, refers broadly to the photodetector itself and any associated optics and/or electronics. For example, signal amplification (photodetector gain) may be provided by a photodetector alone or by a separate signal amplifier that amplifies the output of the photodetector. The light measured by a photodetector may be limited by the use of filters, mirrors, lenses, or other optics. For this reason, "photodetector" is used herein to refer to either a photodector alone or a photodetector with accompanying signal amplifier(s) and optics, if present.

A "detector channel", "detection channel", or "channel" refers to the range of wavelengths that is detected by a specific photodetector. The range of wavelengths detected typically is determined by the use of frequency-dependent filters and/or dichroic mirrors, as is well known in the art. For clarity, the use herein of the term "channel" is distinguished from a secondary use in the field of flow cytometry to refer to a discrete subdivision of the range of intensity values detectable by a single detector.

In some embodiments, a single detector channel is used, wherein the detector channel is defined either by a band-pass filter that transmits light of wavelengths between two threshold wavelengths, or by a long-pass filter that only transmits light of wavelengths longer than some threshold wavelength.

In other embodiments, a plurality of detector channels defined by long-pass filters are used, wherein each transmits light of wavelengths longer than different threshold wavelength, such that the detector channels partially overlap.

In other embodiments, a plurality of non-overlapping detector channels, each defined by a band-pass filter, are used to facilitate the independent measurement of a plurality of spectrally distinct fluorescent dyes. The dyes and detector channels are selected such that, as much as is feasible, the emission maximum of each dye is within a different detector channel, i.e., such that each dye is matched to a detector channel optimized to detect light from that dye. However, due to the breadth of its emission spectrum, light from a given dye may be emitted within one or more other detector channels. The light emitted by a dye within a detector channel other than the detector channel that most closely matches the emission maxima of the dye is referred to herein as "spillover". The detector channel that most closely matches the emission maximum of a dye is referred to herein, with reference to the given dye, as the dye-detection channel or primary channel. All other detector channels are referred to, with reference to the given dye, as spillover channels or secondary channels. A dye and its dye-detection channel will be referred to as "corresponding" or "matched." With reference to a detection channel, the dye that corresponds to the detection channel is referred to as the primary dye; other dyes that emit spillover into the detection channel are referred to as secondary dyes.

As used herein, the term "particles" refers to both to synthetic particles, such as microparticles or beads, and to particles derived from biological sources, such as eukaryotic cells, bacteria, viruses, or macromolecules. As used herein, a "population" of particles refers to a group of particles that possess essentially the same optical properties with respect to the parameters to be measured, such as cells of the same type (cell population), or synthesized beads that, within practical manufacturing tolerances, are of the same size, shape, and composition.

A fluorescent particle is used herein to any particle that exhibits a detectable fluorescence. The particle may be inherently fluorescent, or it may include at least one component that exhibits a detectable fluorescence, or it may be labeled with one or more fluorescent dyes. For example, cells typically are labeled with one or more fluorescent dyes using dye-antibody conjugates that bind to cellular subcomponents to enable detection and analysis, and the labeled cells are examples of fluorescent particles.

The term "MFI", as used herein, refers to the mean or median fluorescence intensity of a population of fluorescence particles. It will be understood that other statistical measures of the population fluorescence, such as truncated mean or truncated median fluorescence, may be used.

A spectrum refers to a continuum of color formed when a beam of white light (or broad-spectrum light source) is dispersed, such as by passage through a prism, so that its component wavelengths are arranged in order. With reference to a broad-spectrum or white-light excitation source, such as a white-light laser, as used herein, the spectrum refers to the continuum of wavelength (color) that is emitted by the excitation source. The "excitation source", as used herein, refers to the light-emitting component, such as a laser, and any associated beam shaping or filtering components, if present. The range of wavelengths emitted by the excitation source as a whole may modified or restricted relative to the range of wavelengths emitted by the light-emitting component alone. For example, the spectrum emitted by a white-light laser may be used in unmodified form, or the spectrum may be restricted by appropriate filtering to provide a spectrum over a desired range of wavelengths.

A table of approximate correspondences of wavelengths and colors in the visible spectrum is provided below.

Table of Color/Wavelengths

| Wavelengths | Color |
| --- | --- |
| 400-420 nm | Violet |
| 420-440 nm | Indigo |
| 440-490 nm | Blue |
| 490-570 nm | Green |
| 570-585 nm | Yellow |
| 585-620 nm | Orange |
| 620-780 nm | Red |

White Light Excitation Source

As used herein, a "white light excitation source" refers to a light source that emits a broad-band, essentially collimated light. Preferred white light excitation sources for use in the present invention are supercontinuum white light lasers.

Supercontinuum white light lasers are available from, for example, Fianium Ltd. (Southampton, UK). Examples include the FemtoPower FP1060 & FP532, the Fianium SC450, the Fianium SC450-8-VE supercontinuum lasers. The Fianium SC450 has 5 W total laser output and has a significant emission range from approximately 450 to 2000 nm. The Fianium SC450-8-VE supercontinuum laser has 8 W of total optical power and over 1.5 W in the visible wavelength range, in a single-mode beam.

Additional examples of supercontinuum white light lasers included the SuperK EXTREME Supercontinuum Fiber Laser Series (NKT Photonics A/S, Birkerød, Denmark), which provides a 400-2400 nm single mode spectrum, and the Koheras SuperK Extreme source with 5 W total laser output (Koheras A/S, Denmark), which provides an approximately 450 to 2000 nm spectrum.

The maximum range of wavelengths provided by the white light excitation source will depend on the range of wavelengths emitted by the laser. The actual range of wavelengths emitted by the white light excitation source may be further restricted using additional filters between the laser and the flow cell.

Color Separation Optics

Dispersion of the broad-spectrum (white-light) excitation source into its spectrum is achieved using color separation optics that includes a dispersion element, such as a prism or diffraction grating, both of which are well known in the art. The dispersion of the excitation beam also results in a spatial expansion (spreading) of the excitation light in one direction, such that the spectrum can be spread out over a detection region that is significantly longer that a particle dimension.

In a preferred embodiment, one or more prisms are used to disperse the white light excitation beam into its constituent spectrum of colors. Prisms will generally disperse light over a much larger frequency bandwidth than diffraction gratings, making them useful for broad-spectrum spectroscopy. Furthermore, prisms, unlike gratings, do not suffer from complications arising from overlapping spectral orders.

A suitable dispersion prism is described in U.S. Pat. No. 4,609,286, incorporated herein by reference.

In a preferred embodiment, the prism system is as described in European Patent Publication EP01403632, incorporated herein by reference. This prism-based cytometry excitation optics system was designed to work with several separate single-color excitation lasers. A set of dispersive prisms redirect the beams different wavelengths so that beams with separated inputs emerge from the final prism substantially overlapping in position an nearly parallel to one another. However, as used in the present invention with a single, broad-spectrum excitation beam, the prism-based cytometry excitation optics system will disperse the broad-spectrum beam into its spectrum, spread out parallel to the flow channel.

Tuneable Filter (TF)

A Tuneable Filter (TF) is a device whose spectral transmission can be electronically controlled by applying voltage, acoustic signal, etc. A variety of tuneable filters are well known in the art. In a preferred embodiment, the tuneable filter is an AcoustoOptical Tuneable Filters (AOTF). An Acousto-Optic Tunable Filter is a solid-state, electronically tunable bandpass filter which uses the acousto-optic interaction inside an anisotropic medium. The transmitted light is controlled using an radio-frequency (RF) frequency applied to the AOTF transducer. The light transmitted through the AOTF can be varied over a complete spectrum by varying the applied frequency corresponding to the wavelength range.

AOTF are available from, for example, Fianium Ltd. (Southampton, UK), Panasonic Industrial Company (Secaucus, N.J.), and Crystal Technology, Inc. (Palo Alto, Calif.). A preferred AOTF is the available as part number 97-02838-01 from Crystal Technology, Inc, which allows selectable transmission over a range of wavelengths from 430-670 nm.

In embodiments that incorporate an AOTF, the actual range of wavelengths emitted by the white light excitation source is restricted by additional filters to be within the range of selectable transmission frequencies provided by the AOTF.

Programmable RF frequency generators capable of generating a rapidly varying RF signal suitable for controlling an AOTF are well known in the art.

Description Based on the Figures

FIGS. 1A-1C

Figure 1B:
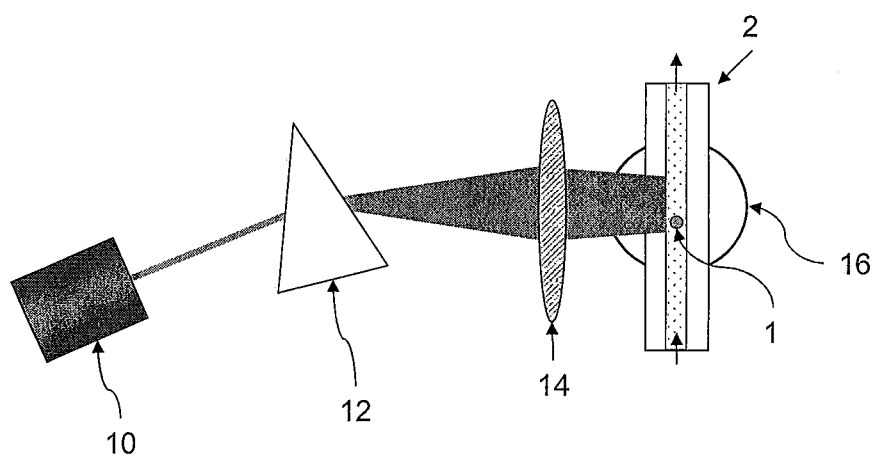
Figure 1C:
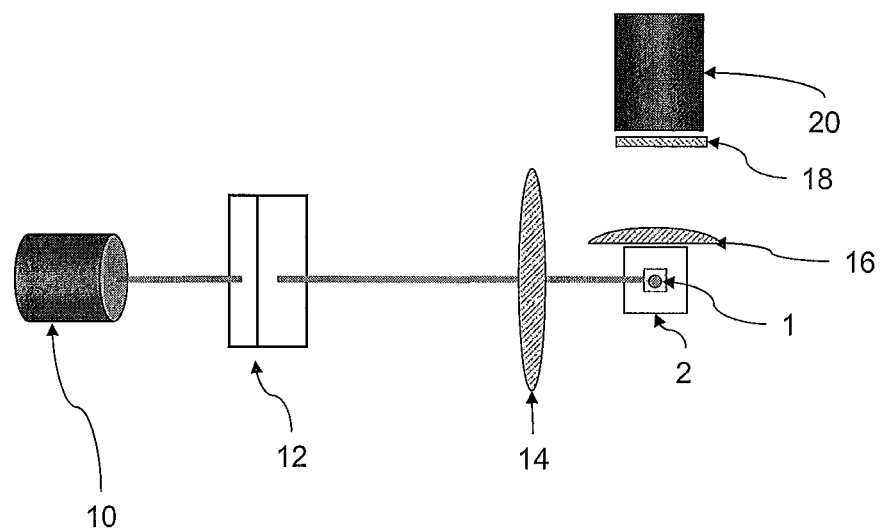

FIGS. 1A-1C depict several views of the components of a system of the present invention. FIG. 1A depicts a side, angled view, FIG. 1B depicts a side view, and FIG. 1C depicts a top view. Not all elements are visible in all views.

Particle 1 (visible in FIGS. 1B and 1C) is carried through a flow channel in cuvette 2. Light from supercontinuum white-light laser 10 is passed through a prism 12 and then focused onto the fluid stream flowing through the flow channel in cuvette 2 by focusing lens 14. The prism disperses the excitation light into its spectrum of colors such that the width of the beam is broadened in a direction parallel to the flow channel. Thus, the wavelength of the excitation light that impinges on particle 1 varies continuously as particle 1 moves through the detection region (the region of the flow channel in cuvette 2 that is exposed to light from laser 10). The prism does not affect the width of the excitation light beam transverse to the flow channel, as shown in the top view of FIG. 1C.

Fluorescence emissions from the particle are collected by lens 16 and directed towards photodetector 20. The diameter of lens 16 is larger that the length of the detection region such that emissions are collected regardless of where the particle is within the detection region. A long-pass filter 18 is oriented in front of photodetector 20. The long-pass filter block is selected to pass only wavelengths longer than the longest wavelength of the excitation light. Thus, the long-pass filter blocks the excitation light from being measured by the photodetector, and allows measurement of the particle emissions essentially without interference from the excitation light.

The detection optics (lens 16, long-pass filter 18, and photodetector 20) are oriented to collect and measure fluorescence light emitted at a right angle from the direction of the excitation beam. Because the intensity of the excitation light is typically much greater than the intensity of fluorescence emissions, and because long-pass filters, in general, are not 100% effective at blocking light outside the selected range of wavelengths, an in-line orientation would suffer from an undesirable level of background signal resulting from excitation light passing through the long-pass filter. By orienting the collection optics such that only fluorescence emissions at right angles to the excitation beam path are measured, this background is minimized. In this configuration, the band-pass filter functions primarily to exclude excitation light that is scattered by the particle at right angles, referred to in flow cytometry as side-scatter.

FIGS. 2A-2C

Figure 2A:
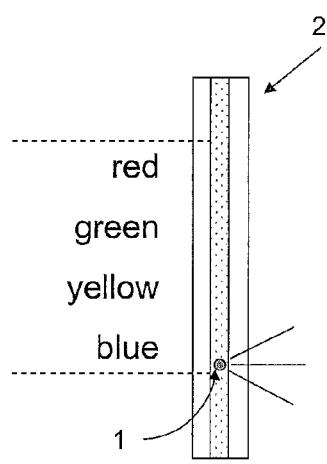
FIGS. 2A, 2B, and 2C depict the passage of a fluorescent particle through a flow channel and the excitation light that illuminates the particle.
Figure 2B:
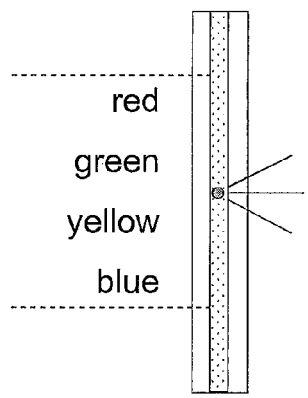
Figure 2C:
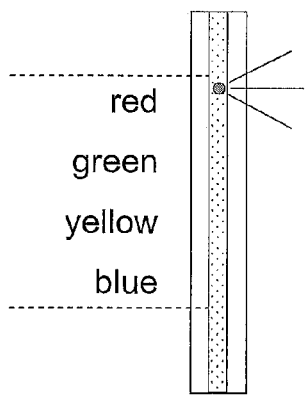

FIGS. 2A-2C depict the use of the system of FIG. 1 to scan the excitation spectrum of a particle. As depicted, the direction of particle 1 (visible in FIGS. 2B and 2C) as it passes through a flow channel in cuvette 2 is from the bottom to the top of the figure. The excitation beam that has been dispersed by the prism into spectrum of colors intersects the flow channel over a length of the channel referred to as the detection region. For illustration purposes, the excitation beam, depicted as the shaded area between the dashed lines, is shown as expanded into a spectrum ranging from a blue light to a red light. The actual range of wavelengths will depend on the range of wavelengths emitted by the excitation source. To facilitate the description, four discrete colors within the excitation beam are indicated, although the excitation beam actually varies continuously from the blue end of its spectrum at the bottom limit of the beam to the red end of its spectrum at the top limit of the beam. Thus, particle 1, as it passes through the detection region of the flow channel, is exposed to the entire spectrum of the excitation light from the blue to the red.

FIG. 2A depicts the start of the spectral scan of a fluorescent particle. The particle has just entered the detection region and is exposed to a wavelength of light that is in the blue end of the excitation beam's spectrum.

FIG. 2B depicts an intermediate stage of the spectral scan. The particle has moved partway through the detection region such that it is exposed to a wavelength of light that is in between yellow and green.

FIG. 2C depicts the end of the spectral scan. The particle has moved to such that it is about to exit the excitation beam. At this point, it is exposed to a wavelength of light that is in the red.

As the particle travels through the detection region and is excited by the continuously varying excitation beam wavelength, fluorescence emissions from the particle, measured in a static band of detection wavelengths, are collected by lens 16 and directed towards photodetector 20 (both elements shown in FIG. 1). The resulting data provide a measure of the excitation spectrum of the particle over the range of wavelengths in the excitation beam.

At any given position within the detection region, particle 1 will be exposed to a small range of wavelengths that depends on the size of the particle, the size of the detection region, and the range of wavelength emitted by the excitation beam. Preferably, the excitation beam spectrum will be spread over a detection region that is significantly larger than the particle size. For example, if excitation beam is spread out by a prism to cover a 1 mm detection region, a cell that is 10 µm in diameters will be exposed to a band of wavelengths that is $\frac{1}{100}^{th}$ of the total excitation spectrum that is dispersed over the detection region. In practice, this can be treated as essentially single-wavelength excitation.

The width of the band of wavelengths that the particle is exposed to any one position can be calculated based on the size of the particle and the rate of change of the excitation wavelength per distance. Let P denote the particle size, let D denote the length of the detection region, which corresponds to the dimension of the expanded excitation beam, and let F1 and F2 denote the shortest and longest wavelength emitted by the excitation source, respectively. The spectrum covers a range wavelengths equal to the absolute value of the difference, |F1−F2|, spread out over a distance D, and the rate of change of the excitation wavelength per distance is |F1−F2|/D. Thus, the particle at a given location within the detection region is exposed to a range of wavelengths that is |F1−F2|/D*P. For example, if the spectrum covers a range of 200 nm, which is spread over a 1 mm detection region, a 10 nm particle will be exposed to only a 2 nm range of excitation light at any one point in the detection region.

FIGS. 3A-C

Figure 3A:
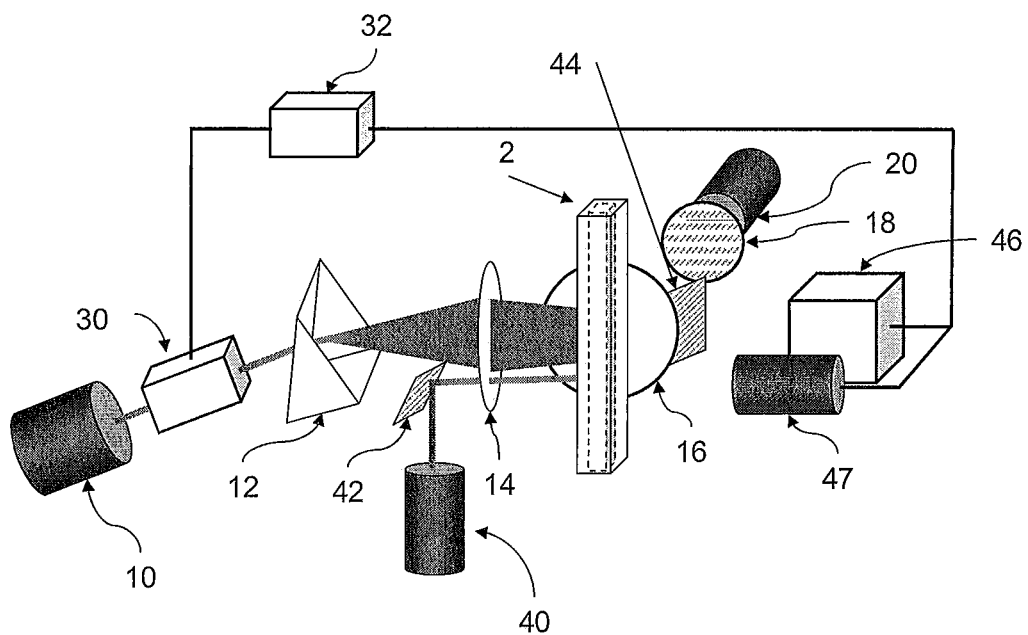
FIGS. 3A, 3B, and 3C depict schematic representations of elements of the optical system of another embodiment of a flow-type particle analyzer of the present invention.
Figure 3B:
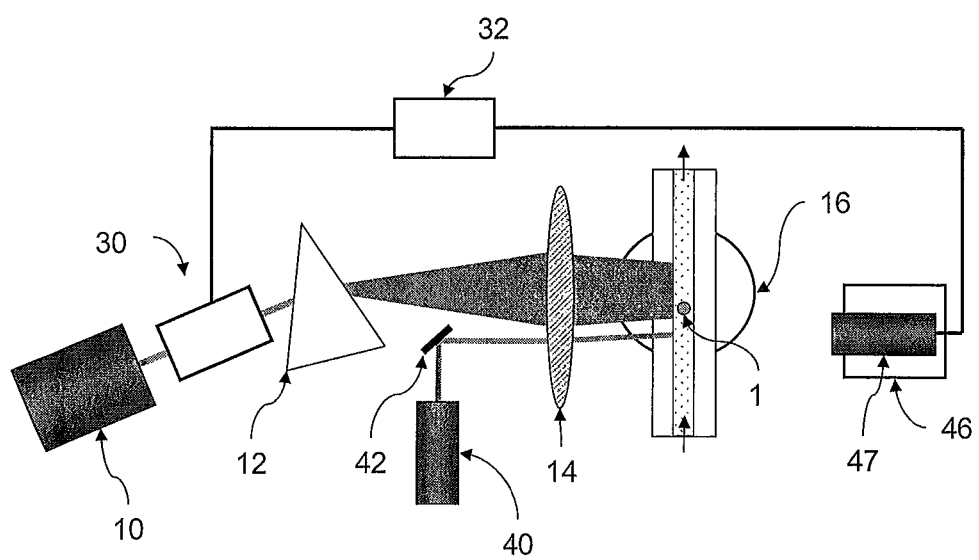
Figure 3C:
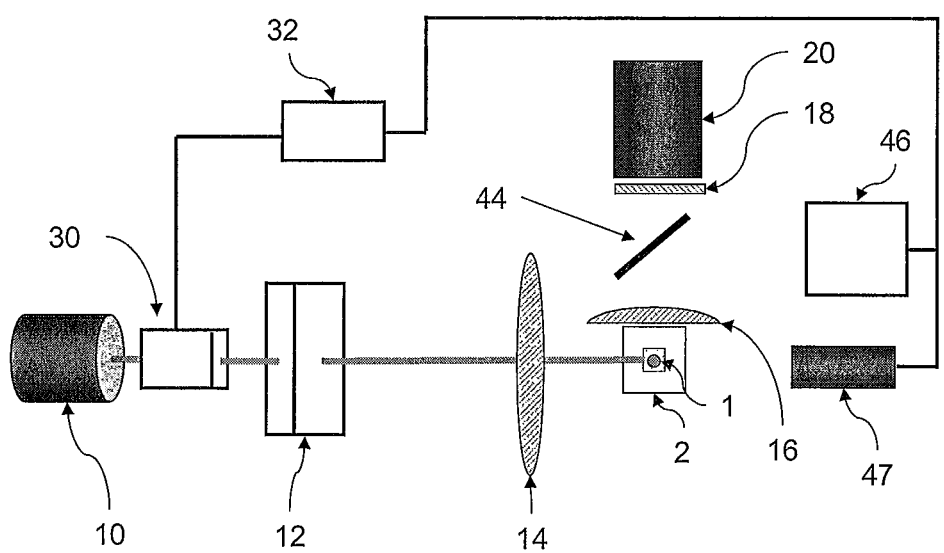

FIGS. 3A-C depict several views of components of an alternative embodiment of a system of the present invention. FIG. 3A depicts a side, angled view, FIG. 3B depicts a side view, and FIG. 3C depicts a top view. Components that are identical to components depicted in FIGS. 1A-C are labeled with the same number. As with FIG. 1, not all elements are visible in all views.

Particle 1 (visible in FIGS. 3B and 3C) is carried through a flow channel in cuvette 2. Light from supercontinuum white-light laser 10 is passed through a prism 12 and then focused onto the fluid stream flowing through the flow channel in cuvette 2 by focusing lens 14. The prism disperses the excitation light into its spectrum of colors such that the wavelength of the excitation light that impinges on particle 1 varies continuously as particle 1 moves through the detection region (the region of the flow channel in cuvette 2 that is exposed to light from laser 10).

Fluorescence emissions from the particle is collected by lens 16 and directed towards photodetector 20. The diameter of lens 16 is larger that the length of the detection region such that emissions are collected regardless of where the particle is within the detection region. A long-pass filter 18 is oriented in front of photodetector 20. The long-pass filter block is selected to pass only wavelengths longer than the longest wavelength of the excitation light. Thus, the long-pass filter blocks the excitation light from being measure by the photodetector, and allows measurement of the particle emissions.

The system of FIG. 3 further comprises a triggering mechanism that allows detection when a particle is about to enter the detection region. Laser 40 emits a beam that is reflected by mirror 42 to be essentially parallel to, but upstream of the excitation beam emitted by white-light laser 10. Laser 40 preferably emits a wavelength of light that is outside the spectrum of laser 10, e.g., a shorter wavelength, but may, alternatively, emit a wavelength that is within the spectrum of laser 10. A particle that is about to enter the detection region is first exposed to the light from laser 40. Photodetector 47 is positioned to measure forward-scatter light. Photodetector array 46 is positioned to measure side-scatter light and fluorescence emissions from particles excited by laser 40.

As shown in the top view (FIG. 3C), the side-scatter and fluorescence emissions from a particle illuminated by laser 40 are collected by lens 16 and reflected toward detector array 46 using mirror 44. Mirror 44 preferably reflects 100% of the light, but is positioned such that only emissions originating from the intersection of the beam from laser 40 with the flow stream are reflected. Light from the spectral scanning detection region misses the mirror and is detected by photodetector 20. Alternatively, mirror 44 may be a dichroic mirror that reflects light of a given range of wavelengths.

Detector array 46 comprises one or more separate detectors that enable the detection of side-scatter light and/or fluorescence emissions. For example, in a preferred embodiment, detector array 46 comprises the detection optics described in U.S. Pat. Nos. 7,129,505 and 6,683,314, both incorporated by reference.

Detector array 46 is configured to measure emissions using detector channels that are distinct from, partially overlapping, or overlapping with the range of frequencies provided by the white light laser. Because the two excitation/detector systems are spatially separated, they are essentially independent. Thus, in general, the spectral scanning of the present invention can be implemented together with the standard excitation and detection optics used in a typical flow cytometer, which may include multiple excitation lasers and multiple detector arrays.

The trigger is used to time the entry of the particle into the detection region. Preferably, the triggering is based on a scatter parameter, e.g., forward scatter, but in practice, any distinguishable signal, such as a fluorescence signal, upstream of the detection region is suitable for triggering.

An Acousto-Optic Tunable Filter (AOTF) 30 is positioned in the path of the excitation beam between laser 10 and the prism 12. AOTF 30 is operably connected to controller 32. AOTF 30 is a bandpass filter that can select and transmit a selected narrow band of wavelengths from the incoming light, under the control of an RF frequency applied to the AOTF by controller 32. To simplify the explanation, the AOTF may be described as selecting a particular wavelength, although it will be understood that the AOTF actually selects a narrow band of wavelengths. Controller 32 is configured to provide a variable RF frequency to the AOTF, thus controlling the selected wavelength.

The width of the dispersed excitation beam filtered to a narrow band of wavelengths corresponds to a fraction of the width of the dispersed, full-spectrum excitation beam. Thus, at a given selected narrow band of wavelengths, only a small spot within the detection region is illuminated, and the location of the spot is determined by angle of dispersion by the prism. As each wavelength is dispersed by the prism at a different angle, varying the selected narrow band of wavelengths from one end of the spectrum to the other results in a concomitant movement of the illuminated spot from one end of the detection region to the other. The controller 32 is configured to change the narrow band of wavelengths selected by the AOTF in synchrony with the movement of the particle through the flow channel such that the particle is illuminated continuously as it passes through the detection region, albeit with a constantly varying wavelength of excitation light.

In order to synchronize the change in wavelength selected by the AOTF with the movement of the particle through the flow channel, the wavelength selection must be synchronized with the entry of the particle into the detection region, and the rate of change of the wavelength selection must be synchronized with the speed of the particle through the detection region. Entry of a particle into the detection region is timed by from the trigger signal (e.g., forward-scatter) obtained from the particle passing through the trigger laser beam just upstream of the detection region. The trigger signal is sent from detector 47 or 46 (depending on which is used as the trigger signal) to controller 32, which the initiates a sweep through the RF signal that controls the AOTF's sweep through the selected wavelengths.

The time from the detection of the trigger to the initiation of the spectral sweep depends on the flow rate and distance from the trigger detection region to the spectral-scanning detection region. In practice, the system can be calibrated empirically.

Controller 32 is configured to change of the wavelength selected by the AOTF such that the movement of the illuminated spot with the detection region moves at the same speed as the particle. The speed of the particle (i.e., speed of the flow stream through the cuvette 2) is instrument-dependent, and can be determined empirically using methods that are standard in the field of flow cytometry.

FIGS. 4A-D

FIGS. 4A-D depict the use of the system of FIG. 3 to scan the excitation spectrum of a particle. As depicted, the direction of particle 1 as it passes through a flow channel in cuvette 2 is from the bottom to the top of the figure. The excitation beam that has been dispersed by the prism into spectrum of colors intersects the flow channel over a length of the channel referred to as the detection region. For illustration purposes, the excitation beam is shown as expanded into a spectrum ranging from a blue light to a red light. The actual range of wavelengths will depend on the range of wavelengths emitted by the excitation source. To facilitate the description, four discrete colors within the excitation beam are indicated, although the excitation beam actually varies continuously from the blue end of its spectrum at the bottom limit of the beam to the red end of its spectrum at the top limit of the beam. Thus, particle 1, as it passes through the detection region of the flow channel, is exposed to the entire spectrum of the excitation light from the blue to the red.

Figure 4A:
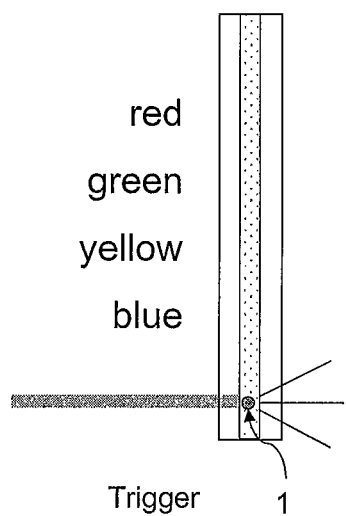
FIGS. 4A, 4B, 4C, and 4D depict the passage of a fluorescent particle through a flow channel and the excitation light that illuminates the particle.

FIG. 4A depicts the detection of the particle by the forward-detector, 47. The detection of the particle by the forward-scatter detector provides the trigger that indicates that particle 1 is about to enter the spectral-scanning detection region.

Figure 4B:
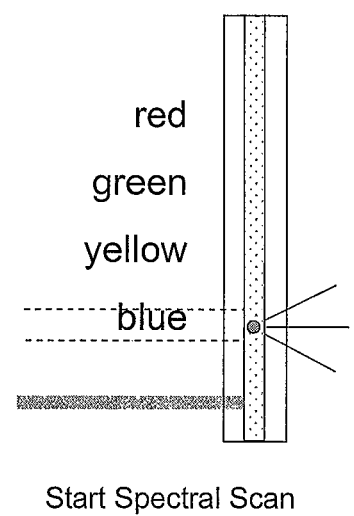

FIG. 4B depicts the start of the spectral scan of a the fluorescent particle. The particle has just entered the detection region and is exposed to a wavelength of light that is in the blue end of the excitation beam's spectrum. The full excitation beam is filtered by the Acousto-Optic Tunable Filter (AOTF) 30 to provide a narrow band of excitation light at the shortest wavelength (approximately blue) in the spectrum of the full excitation beam. The narrow band of the filtered excitation beam is depicted as the shaded area between the dashed lines. Because the blue end of the excitation beam spectrum is dispersed at the greatest angle and forms the limit of the detection region, the narrow band intersects the flow stream at the beginning of the detection region.

Figure 4C:
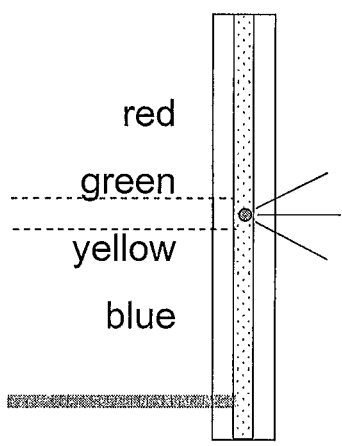

FIG. 4C depicts an intermediate stage of the spectral scan. The particle has moved partway through the detection region such that it is positioned in the detection region where a wavelength of light that is in between yellow and green intersects the flow stream. The narrow band of wavelengths selected by the AOTF has been changed in synchrony with the particle movement such that the particle is illuminated with a wavelength within this narrow band, and the other wavelengths within the full spectrum of the excitation beam have been filtered out.

Figure 4D:
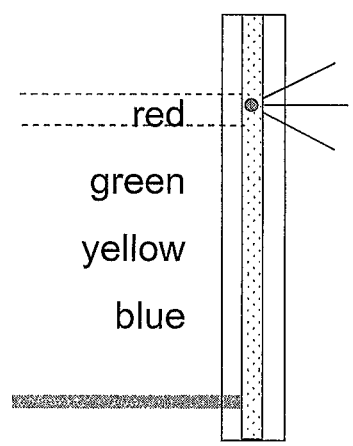

FIG. 4D depicts the end of the spectral scan. The particle has moved to such that it is about to exit the excitation beam. At this point, the particle is positioned in the detection region where a wavelength of light that is approximately red intersects the flow stream. The narrow band of wavelengths selected by the AOTF has been changed in synchrony with the particle movement such that the particle is illuminated with a wavelength within this narrow band, and the other wavelengths within the full spectrum of the excitation beam have been filtered out.

Thus, as described above, as the particle travels through the detection region, it is excited by the continuously varying excitation beam having a narrow band of wavelengths. The narrow excitation beam tracks the particle through the detection region. The physical movement of the excitation beam results from wavelength-dependent dispersion by the prism and the continuously varying wavelength selection by the AOTF.

As the particle travels through the detection region and is excited by the continuously varying excitation beam wavelength, fluorescence emissions from the particle, measured in a static band of detection wavelengths, are collected by lens 16 and directed towards photodetector 20 (both elements shown in FIG. 3). The resulting data provide a measure of the excitation spectrum of the particle over the range of wavelengths in the excitation beam.

FIG. 5

Figure 5:
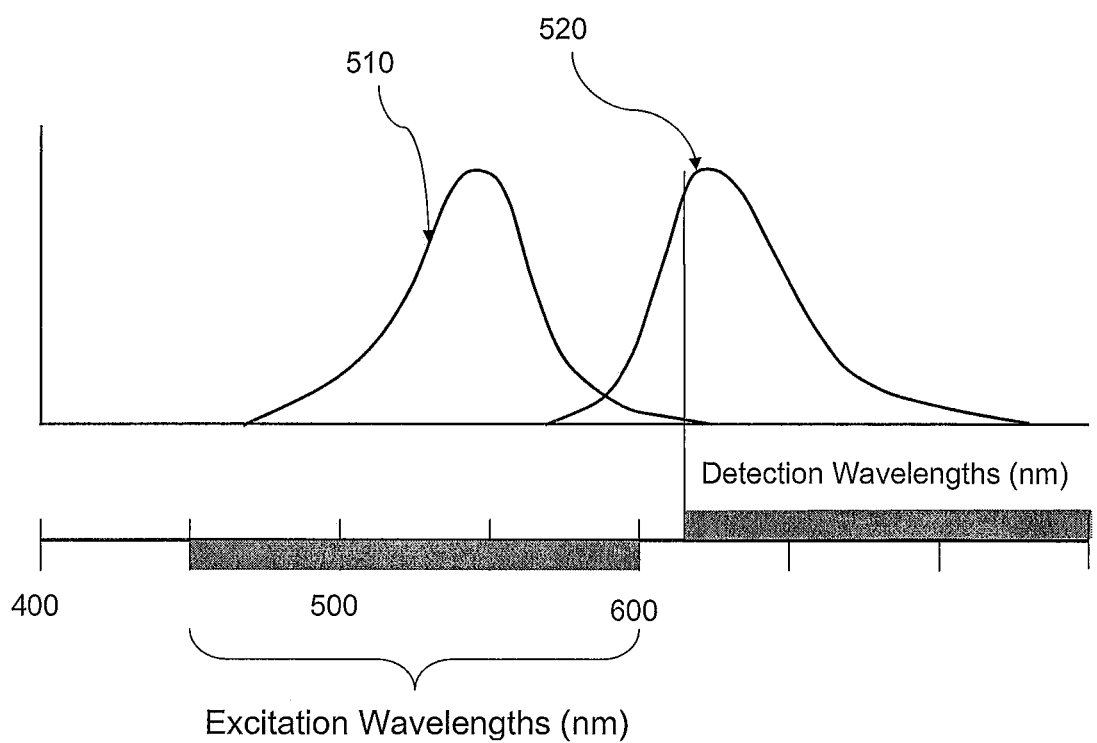
FIG. 5 depicts the relationship between the excitation and emission spectra of a fluorescent particle, the spectrum of the excitation light source use to excite the particle, and the detection channel used to detect particle emissions.

FIG. 5 depicts the excitation beam spectrum and the detector channel of one embodiment of the present invention, along with the excitation and emission spectra of a exemplary fluorescent particle, referred to herein as FP1. The excitation spectrum 510 and emission spectrum 520 of FP1 are shown for illustrative purposes only, to aid in understanding the invention, and are not meant to represent the spectra of any particular fluorescent dye. The x-axis is wavelength, and the y axis is an arbitrary scale used to exemplify the normalized spectra. In this example, the fluorescent particle exhibits an excitation peak at about 550 nm and an emission peak at about 625 nm (Stokes' shift of 75 nm).

The limits of the excitation beam spectrum (range of wavelengths emitted by the excitation source) and the detection channel (range of wavelengths used for the detection of particle fluorescence) are shown schematically as bars along the x-axis. In this example, it is assumed that the spectrum of the excitation beam ranges from 450 to 600 nm, which corresponds to a range in color from a blue to an orange (see table, below). The detector channel, which is defined by the transmission range of a long-pass filter (e.g., filter 18, shown in FIGS. 1 and 3), detects emissions of wavelength longer than about 630 mm.

As can be seen in FIG. 5, the detector channel measures the emissions over a significant portion of the total emission spectrum of the fluorescent particle, FP1. As the particle moves through the flow channel and is excited by a constantly changing excitation wavelength, the emissions from the particle are measured in the detector channel. In this example, the sweep through the spectrum of the excitation source provides essentially a scan of the full excitation spectrum of FP1, as the excitation spectrum of the FP1 is largely encompassed within the range of wavelengths provided by the excitation beam source.

The use of a long-pass filter typically is preferable to the use of a band-pass filter because it maximizes the amount of fluorescence emission measured, although either can be used.

The long-pass filter that defines the detection channel excludes excitation light from reaching the detector. Because the detector channel is clearly separated from the excitation beam spectra, the excitation beam can be on at all times. Thus, embodiment shown in FIG. 5 can be used with either the instrument and methods shown in FIGS. 1 and 2, or the instrument and methods shown in 3 and 4.

FIG. 6

Figure 6:
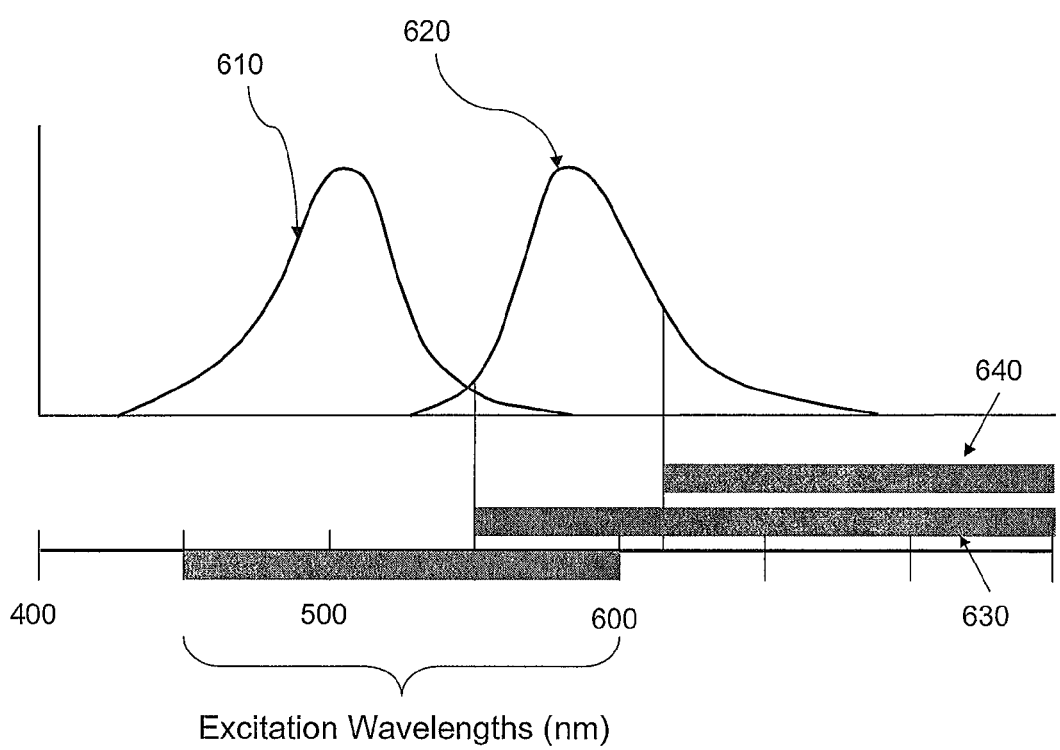
FIG. 6 depicts the relationship between the excitation and emission spectra of a fluorescent particle, the spectrum of the excitation light source use to excite the particle, and two overlapping (staggered) detection channels used to detect particle emissions.

FIG. 6 depicts the excitation beam spectrum and the detector channel of another embodiment of the present invention, along with the excitation and emission spectra of a second exemplary fluorescent particle, referred to herein as FP2. The excitation spectrum 610 and emission spectrum 620 of FP2 are shown for illustrative purposes only, to aid in understanding the invention, and are not meant to represent the spectra of any particular fluorescent dye. The x-axis is wavelength, and the y axis is an arbitrary scale used to exemplify the normalized spectra. In this example, the fluorescent particle exhibits an excitation peak at about 510 nm and an emission peak at about 585 nm (Stokes' shift of 75 nm).

The limits of the excitation beam spectrum (range of wavelengths emitted by the excitation source) and the detection channel (range of wavelengths used for the detection of particle fluorescence) are shown schematically as bars along the x-axis, below the particle spectra. In this example, it is assumed that the spectrum of the excitation beam ranges from 450 to 600 nm. The first detection channel, 640, is identical to that of FIG. 5, and detects emissions of wavelength longer than about 630 nm. A second detection channel, 630, defined by a second long-pass filter, detects all emissions of wavelength longer than about 550 nm. Thus, the second long-pass filter excludes only excitation light below 550 nm in wavelength from reaching the detector.

As can be seen in FIG. 6, the emission maximum of FP2 is well to the left of the wavelength cutoff for detector channel 640, and the fraction of the total emission of FP2 that falls within detector channel 640 is only a small portion of the total emission spectrum of FP2. Although the emission from FP2 can be measured using detector channel 640, the detection sensitivity is expected to be reduced because most of the emission from FP2 is blocked by the long-pass filter.

The second detector channel, 630, detects emissions of wavelength longer than about 550 nm, and is configured to detect almost all the light emitted by FP2. However, detection channel 630 overlaps the emission spectrum of the excitation beam. Thus, if the full spectrum of the excitation beam were to be continually illuminating the flow channel, scatter from the portion of the excitation beam spectrum that overlaps detection channel 630 would interfere with the detection of FP2 fluorescence in that channel.

The detection scheme shown in FIG. 6 preferably is used with the instrument and methods shown in FIGS. 3 and 4. As described above, as the particle moves through the flow channel and is excited by a constantly changing excitation wavelength, only an essentially single wavelength is shining on the particle at any one time. The excitation beam sweeps from a wavelength of about 450 nm to about 600 nm, tracking the movement of the particle. During this sweep, while the excitation beam is under the wavelength cutoff of detection channel 630, there is no excitation beam light that can scatter and compete with the detection of FP2 fluorescence. Thus, detection channel 630 can be used to detect the emission from FP2 during a scan of the FP2 excitation spectrum over the range of 450-550 nm.

Once the excitation beam has reached the threshold of detection channel 630, detection channel 630 is no longer used to measure the emissions from FP2. However, detection channel 640 is still useable for detecting the emissions from FP2. The signal from FP2 emissions measure in detection channel 640 preferably are amplified to compensate for the lower detection sensitivity. Thus, the excitation spectrum of FP2 can be scanned over the full excitation beam spectrum, measured either in detection channel 640 (with lower sensitivity), or piecewise using detection channel 630 (with high sensitivity) over the range 450-550 nm, followed by completing the scan using detection channel 640 (with lower sensitivity).

FIG. 6 describes a detection scheme using two overlapping detector channels to enable scanning excitation spectra with higher specificity over a broader range. Clearly, additional detector channels can be used. Each detection channel can increase the range of the excitation spectrum scan that is carried out with highly efficient detection of the emissions.

The multiple detector channels need not be overlapping. For example, detector channel 630 could also be defined by a band-pass filter that transmits light between 550 and 630 nm, which is the start of the next detector channel.

The detection scheme shown in FIG. 6 is also suitable for measuring the excitation spectrum of other fluorescent particles, such as FP1, described above and shown in FIG. 5. To measure the excitation spectrum of FP1, detection channel 630 either can be ignored, or can be used to improve the measurement of the emission of FP1 during the first portion of the excitation scan. In general, by providing a set of staggered detection channels, the excitation spectrum of any fluorescent particles that has an excitation spectrum overlapping the spectrum of the white light laser can be measured. The information from the separate detection channels preferably is combined to obtain the most sensitive measurement of the dye emissions while the excitation light is varied across the spectrum.

FIG. 7

Figure 7:
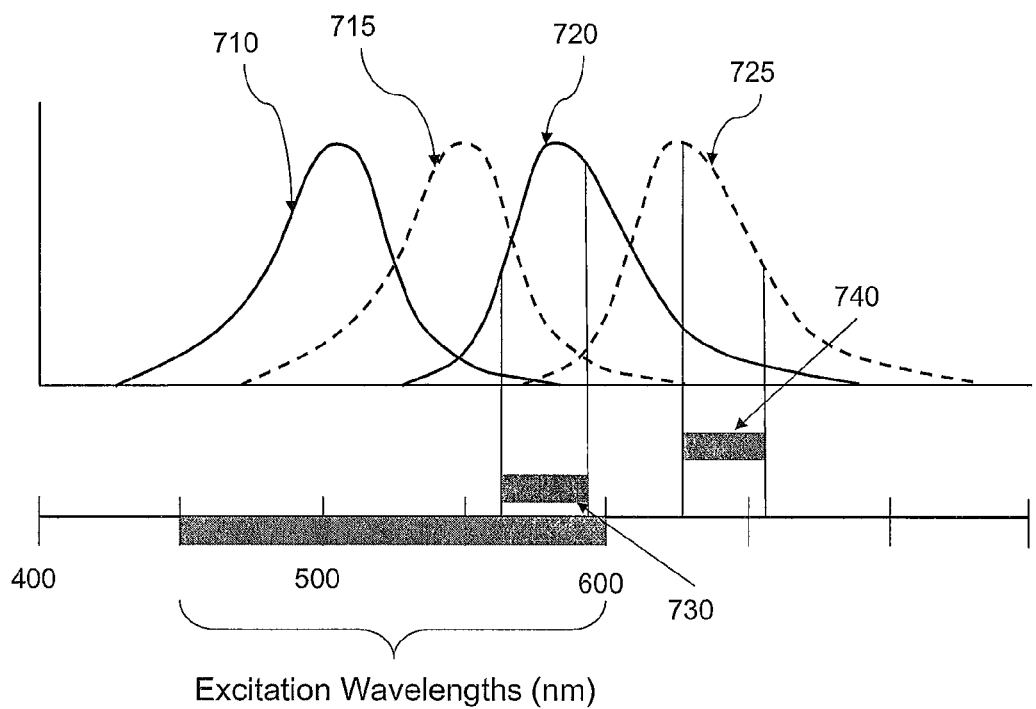
FIG. 7 depicts the relationship between the excitation and emission spectra of a fluorescent particle, the spectrum of the excitation light source use to excite the particle, and two non-overlapping detection channels used to detect particle emissions, wherein each detection channel is selected to correspond approximately to the excitation maxima of a different dye.

FIG. 7 depicts the excitation beam spectrum and the detector channels of another embodiment of the present invention, along with the excitation and emission spectra of a second exemplary fluorescent particle, referred to herein as FP2, and the excitation and emission spectra of a third exemplary fluorescent particle, referred to herein as FP3. The excitation spectrum 710 and emission spectrum 720 of FP2 and the excitation spectrum 715 and emission spectrum 725 of FP3 are shown for illustrative purposes only, to aid in understanding the invention, and are not meant to represent the spectra of any particular fluorescent dye. The x-axis is wavelength, and the y axis is an arbitrary scale used to exemplify the normalized spectra. In this example, the fluorescent particle, FP2, exhibits an excitation peak at about 510 nm and an emission peak at about 585 nm (Stokes' shift of 75 nm), and the fluorescent particle, FP3, exhibits an excitation peak at about 550 nm and an emission peak at about 625 nm (Stokes' shift of 75 nm).

The limits of the excitation beam spectrum (range of wavelengths emitted by the excitation source) and the detection channel (range of wavelengths used for the detection of particle fluorescence) are shown schematically as bars along the x-axis, below the particle spectra. In this example, it is assumed that the spectrum of the excitation beam ranges from 450 to 600 nm. The first detection channel, 730, defined by a band-pass filter, detects emissions of wavelength over a range of about 560-590 nm. This first detection channel corresponds approximately to the emission maximum of FP2, with the upper wavelength boundary selected so as to avoid encompassing significant emission from FP3. This first detection channel is also referred to as the FP2-channel. The second detection channel, 740, defined by a second band-pass filter, detects emissions of wavelength over a range of about 625-710 nm. This second detection channel corresponds approximately to the emission maximum of FP3, with the lower wavelength boundary selected so as to avoid encompassing significant emission from FP2. This second detection channel is also referred to as the FP3-channel.

As can be seen in FIG. 7, the FP2-channel measures a significant fraction of the emissions of FP2, but measures on a small faction of the emissions of FP3. Similarly, the FP3-channel measures a significant fraction of the emissions of FP3, but measures on a small faction of the emissions of FP2. The selection of the two detection channels to correspond to the two dye excitation maxima enables relatively independent measurement of the two dye emissions, which further enables relatively independent measurement of the two dye excitation spectra.

The detection scheme shown in FIG. 7 preferably is used with the instrument and methods shown in FIGS. 3A-C and 4A-D. As described above, as the particle moves through the flow channel and is excited by a constantly changing excitation wavelength, only an essentially single wavelength is shining on the particle at any one time. The excitation beam sweeps from a wavelength of about 450 nm to about 600 nm, tracking the movement of the particle. During this sweep, while the excitation beam wavelength is under the wavelength of the FP2-detection channel 730, there is no excitation beam light that can scatter and compete with the detection of FP2 fluorescence. Thus, the FP2-detection channel 730 can be used to detect the emission from FP2 during a scan of the FP2 excitation spectrum over the range of 450-560 nm, which represents most of the range of wavelengths over which FP2 exhibits significant excitation.

Because the FP3-channel is outside the range of the excitation light wavelengths, no scattered excitation beam light is detected in the FP3-channel. Thus, the FP3-detection channel 740 can be used to detect the emission from FP3 during a scan of the FP3 excitation spectrum over the full sweep of excitation light wavelengths. Because the excitation spectrum of FP3 extends beyond the range of excitation light wavelengths. this provides a significant portion of, but not all of, the excitation spectrum of FP3.

FIG. 7 describes an example of a detection scheme using detector channels that are matched to the particular dyes that will be used in the assay. The selection of the detection channels that correspond to the dye excitation maxima enables relatively independent measurement of the dye emissions, which further enables relatively independent measurement of the dye excitation spectra. Although two dyes are shown in FIG. 7, this detection scheme can be applied to the analysis of a higher number of spectrally distinct dyes by using a correspondingly higher number of detection channels, each matched to the emissions of a particular dye.

An advantage of this embodiment of the invention is that it facilitates that analysis of particles labeled with multiple dyes. For example, as is typically the case in cell analysis by flow cytometry, a cell may be labeled with a number of distinct dyes, each bound to a different cellular protein. The multiply labeled cell will exhibit a total excitation spectrum that results from the combination of the dyes. By using detectors that are matched to the individual dyes and, therefore, enable relatively independent measurements of the dye emissions, the excitation spectrum can be separated more easily into its components corresponding to the excitation spectrum of each of the dyes in the combination.

Methods for mathematically separating (deconvolving) a spectrum that is the convolution of a plurality of spectra into the component spectra are known in the art (see, for example, Robinson et al. supra). Such methods can be used to calculate the contribution from each of component dyes in the present methods and, thus, to identify the labels present on a particle, such as a cell.

We claim:

1. A flow-type particle analyzer, the flow-type particle analyzer comprising:
   a) an excitation light source that emits a collimated broad-spectrum excitation light beam,
   b) a cuvette channel,
   c) a dispersion element positioned between the excitation light source and the cuvette channel that disperses the spectrum of the excitation light beam to produce a continuous spectrum of continuously varying wavelengths of the excitation light beam on said cuvette channel such that a fluoresecent particle passing through a detection region of said cuvette channel in a fluid stream will traverse the continuous spectrum of continuously varying wavelengths of the excitation light beam; and
   d) detection optics that measure light emitted from fluorescent particles passing through the continuous spectrum of continuously varying wavelengths in the detection region of said cuvette channel.

2. The flow-type particle analyzer of claim 1, further comprising an optical cuvette having said cuvette channel extending through said optical cuvette.

3. The flow-type particle analyzer of claim 1, wherein said excitation light source contains a white-light laser.

4. The flow-type particle analyzer of claim 3, wherein said excitation light source further contains filter elements that restrict the range of wavelengths emitted by the white-light laser.

5. The flow-type particle analyzer of claim 1, wherein said detection optics comprises a photodetector configured to measure a range of wavelengths that are longer than the wavelengths in the excitation light spectrum that is directed onto the detection region.

6. The flow-type particle analyzer of claim 1, further comprising a tuneable filter positioned in the excitation light beam between the excitation light source and the dispersion element, configured to allow selection of a narrow band of wavelengths that is passed by the filter, wherein said selection is under the control of a controller.

7. The flow-type particle analyzer of claim 1, wherein the detection optics are configured to obtain an emission spectrum produced by fluorescent particles in the detection region.

8. The flow-type particle analyzer of claim 7, wherein the emission spectrum is at least a significant portion of the total emission spectrum produced by particles in the detection region.

9. The flow-type particle analyzer of claim 7, where the detection optics comprise a long-pass filter.

10. The flow-type particle analyzer of claim 7, where the detection optics comprise a single detector.

11. The flow-type particle analyzer of claim 10, where the single detector is a broad-band detector.

12. The flow-type particle analyzer of claim 1, wherein said detection optics includes a filter that excludes light of wavelengths that overlap the range of wavelengths provided in the excitation light spectrum that is directed onto the detection region.

13. The flow-type particle analyzer of claim 1, wherein said detection optics comprises a plurality of photodetectors, each photodetector containing a filter that excludes light of wavelengths that overlap the range of wavelengths provided in the excitation light spectrum that is directed onto the detection region.

14. The flow-type particle analyzer of claim 1, wherein said detection optics comprises a plurality of photodetectors, each configured to measure a range of wavelengths that are longer than at least a portion of the wavelengths in the excitation light spectrum that is directed onto the detection region.

15. The flow-type particle analyzer of claim 1, wherein said detection optics comprises a plurality of photodetectors, each configured to measure a range of wavelengths defined by a bandpass filter, wherein the ranges of wavelengths measured by said plurality of photodetectors do not overlap.

* * * * *